United States Patent [19]
Cole et al.

[11] Patent Number: 5,662,690
[45] Date of Patent: Sep. 2, 1997

[54] DEFIBRILLATOR WITH TRAINING FEATURES AND PAUSE ACTUATOR

[75] Inventors: Clinton Cole, Seattle; Carlton B. Morgan, Bainbridge Island; Judi Cyrus, Preston; Daniel Powers, Bainbridge Island, all of Wash.

[73] Assignee: Heartstream, Inc., Seattle, Wash.

[21] Appl. No.: 672,739

[22] Filed: Jun. 28, 1996

Related U.S. Application Data

[63] Continuation of Ser. No. 351,897, Dec. 8, 1994, Pat. No. 5,611,815.

[51] Int. Cl.$^6$ .................................................. A61N 1/39
[52] U.S. Cl. ............................................................ 607/5
[58] Field of Search ........................................... 607/5, 7

[56] References Cited

U.S. PATENT DOCUMENTS

| | | | |
|---|---|---|---|
| 3,453,745 | 7/1969 | Spivak | 35/17 |
| 3,747,605 | 7/1973 | Cook | 607/17 |
| 4,489,387 | 12/1984 | Lamb et al. | 128/630 |
| 4,610,254 | 9/1986 | Morgan et al. | 607/6 |
| 4,827,936 | 5/1989 | Pless et al. | 607/4 |
| 5,097,830 | 3/1992 | Eikefjord et al. | 607/8 |
| 5,137,458 | 8/1992 | Ungs et al. | 434/262 |
| 5,179,945 | 1/1993 | Van Hofwegen et al. | 607/5 |
| 5,275,572 | 1/1994 | Ungs et al. | 434/265 |
| 5,284,135 | 2/1994 | Lopin | 607/4 |
| 5,391,187 | 2/1995 | Freeman | 607/5 |
| 5,421,830 | 6/1995 | Epstein et al. | 607/30 |
| 5,443,490 | 8/1995 | Flugstad | 607/5 |
| 5,474,574 | 12/1995 | Payne et al. | 607/7 |

FOREIGN PATENT DOCUMENTS

| | | | |
|---|---|---|---|
| 0499744 A2 | 9/1991 | European Pat. Off. | G08Q 23/38 |
| 0546666 A2 | 6/1993 | European Pat. Off. | A61N 1/39 |
| 4337110 | 11/1994 | Germany | G06F 15/42 |

OTHER PUBLICATIONS

Product brochure for VIVALinkAED Automatic External Defibrillator System (4 pp.).

*Primary Examiner*—William E. Kamm
*Assistant Examiner*—Carl H. Layno
*Attorney, Agent, or Firm*—James R. Shay; Cecily Anne Snyder

[57] ABSTRACT

A defibrillator featuring a treatment mode and a training mode comprises an energy source, an electrode connector, a controller, and training mode circuitry. The controller comprises a feature for connecting the energy source to the electrode connector and a pause actuator for permitting a user to inhibit electrical stimulation when no longer required. The training mode circuitry simulates the operation of the defibrillator in treatment mode. The defibrillator also includes a method of operating comprising the steps of: 1) providing a defibrillator having an energy source, a controller, and electrode connectors, wherein the controller further comprises circuits for actuating the defibrillator to deliver a defibrillation shock from the defibrillation energy source to the electrode connectors and 2) operating the defibrillator in a training mode to simulate delivery of a defibrillation shock from the energy source to the electrode connectors without delivering a defibrillation shock from the energy source to the electrode connectors.

9 Claims, 4 Drawing Sheets

DEFIBRILLATOR WITH TRAINING FEATURES AND PAUSE ACTUATOR

This application is a CONTINUATION of application Ser. No. 08/351,897 filed 08 Dec. 1994, now U.S. Pat. No. 5,611,815 issued Mar. 18, 1997.

BACKGROUND OF THE INVENTION

This invention relates to defibrillators, particularly semiautomatic and automatic external defibrillators, having built-in training features. The invention also relates to defibrillator features that facilitate training and use of the defibrillator.

One frequent consequence of heart attacks is the development of cardiac arrest associated with a heart arrhythmia, such as ventricular fibrillation. Ventricular fibrillation may be treated by applying an electric shock to the patient's heart through the use of a defibrillator. The chances of surviving a heart attack decrease with time after the attack. Quick response to a heart attack by administering a defibrillating shock as soon as possible after the onset of ventricular fibrillation is therefore often critically important.

Training potential defibrillator operators on the proper use of a defibrillator can reduce defibrillator deployment time. The prior art has therefore developed two different approaches to defibrillator operator training. In the first approach, the trainee actually operates the defibrillator as if delivering an electrical shock to treat a patient instead of delivering the shock to a live patient, however, the defibrillator delivers the shock to a patient simulator, such as a mannequin or an electronic device. See, e.g., Ungs et al. U.S. Pat. No. 5,275,572.

In the second approach, the trainee does not use an actual defibrillator at all. Instead, training is conducted on a separate training device which looks like a defibrillator and simulates the operation of a defibrillator. The training device cannot actually be used to deliver a defibrillation shock to a patient, however. Medical organizations following this defibrillator training approach must therefore have two sets of instruments, one for training and one for actual use.

SUMMARY OF THE INVENTION

Prior art defibrillators and defibrillator training techniques were directed to emergency medical personnel who use defibrillators relatively frequently and can therefore maintain their defibrillator use skills. As the use of defibrillators by police, firefighters and other non-medical personnel becomes more common (i.e., as the ratio of defibrillators to patients increases), the use frequency of each defibrillator by each potential defibrillator operator decreases. The defibrillator must therefore be easy to use, and defibrillator operation must be easy to train. Moreover, since more people will need to be trained, training costs per person must be kept at a minimum.

This invention is a defibrillator with built-in training features. In a preferred embodiment, the invention is a defibrillator having a treatment mode and a training mode, comprising an energy source; an electrode connector; a controller, the controller comprising means for connecting the energy source to the electrode connector; and training mode means for simulating the operation of the defibrillator in treatment mode.

The invention also includes a method of operating a defibrillator comprising steps of providing a defibrillator comprising a defibrillation energy source, a controller and electrode connectors, the controller comprising means for actuating the defibrillator to deliver a defibrillation shock from the defibrillation energy source to the electrode connectors and operating the defibrillator in a training mode to simulate delivery of a defibrillation shock from the energy source to the electrode connectors without delivering a defibrillation shock from the energy source to the electrode connectors.

The invention will be described in more detail below with reference to the drawings.

DETAILED DESCRIPTION OF THE PREFERRED EMBODIMENT

Defibrillators fall into three general categories. Manual defibrillators charge and deliver shocks to patients solely in response to user actuation or a user request. Automatic defibrillators charge and deliver shocks to patients solely in response to ECG data collected from the patient and analyzed by the defibrillator. Semiautomatic defibrillators analyze patient ECG data and recommend shocks (or recommend that no shock be delivered) but require user actuation to deliver the shock to the patient. This invention may be implemented in all three kinds of defibrillators.

Figure 1:
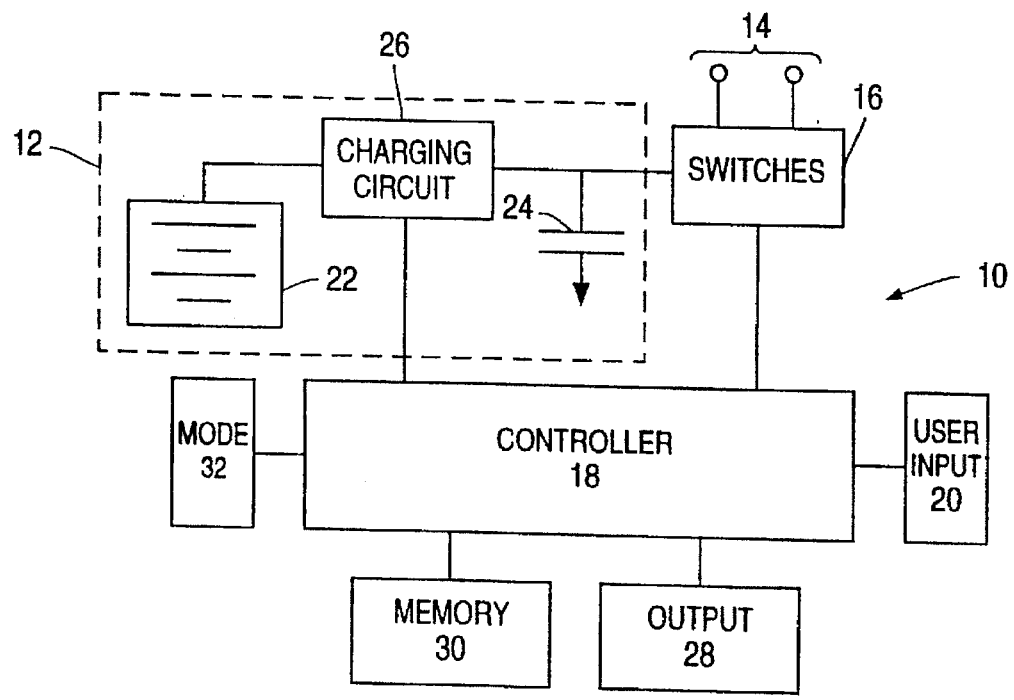
FIG. 1 is a schematic block diagram of a defibrillator for use with this invention.

FIG. 1 is a schematic representation of a defibrillator, which may be manual, semi-automatic or automatic. Defibrillator 10 has an energy source 12, electrode connectors 14, and switches 16 between the energy source and the electrode connectors. Energy source 12 may be made up of an energy storage medium 22 (e.g., a battery), a capacitor or capacitor bank 24, and a charging circuit 26.

A controller 18 (such as a microprocessor) within defibrillator 10 controls the operation of energy source 12 and switches 16 to deliver an electrical pulse to electrode connectors 14. Controller 18 receives input through a user input 20, which may be, e.g., one or more buttons or other actuators, one or more digital or analog ports, or combinations thereof. Controller 18 also sends out information through output 28 which may include a display, digital or analog ports, or combinations thereof. If the defibrillator is automatic or semiautomatic, controller 18 includes an ECG signal analyzer. Defibrillator 10 also has a memory 30 for storing digital and/or analog information.

Defibrillator 10 may be used to deliver an electrical pulse or shock to a patient. For example, if defibrillator 10 is a semi-automatic defibrillator, it may be used as follows. First, the user attaches electrodes at one end to electrode connectors 14 and at their other end to a patient. The ECG analyzer of the defibrillator controller 18 then analyzes ECG signals obtained through the electrodes to determine whether it is advisable to deliver a shock to the patient. The defibrillator displays its shock/no shock advice on output 28. If a shock is advised and the user decides to deliver a shock, then the user may actuate the controller through user input 20 to deliver the shock.

The user's decision of whether or not to actuate the defibrillator to deliver a shock to the patient may depend on more than the defibrillator's shock/no shock recommendation. For example, if the patient is conscious, then the user will likely ignore a shock recommendation. Also, the defibrillator may provide more detailed information than the simple shock/no shock recommendation, such as information on the quality of the electrical connection between the electrodes and the patient. The defibrillator may also display the actual ECG waveforms. This information and other information from the defibrillator, the patient or the surrounding circumstances can affect how the user should operate the defibrillator to provide the most effective care for the patient. Defibrillator users should therefore be trained on the operation of the defibrillator and on the best responses to different patient treatment scenarios.

The defibrillator of this invention may be operated in at least two different modes. The first is the patient treatment mode, described above. The second mode is a training mode in which the defibrillator operates as if there were a patient present and requiring treatment. In the training mode, however, there is no patient providing ECG signals, and the defibrillator does not deliver any electrical pulse from the energy source to the electrode connectors.

The defibrillator 10 shown schematically in FIG. 1 may be switched from a patient treatment mode to a training mode through the use of defibrillator operation mode control 32. When switched to training mode, controller 18 simulates the operation of the defibrillator for treating a patient by simulating the collection of patient ECG data (e.g., by retrieving a stored patient ECG waveform from memory 30) and simulating the delivery of an electrical pulse to the patient in response to actuation by the trainee.

When switched to training mode, controller 18 also preferably disables energy source 12 so that capacitor 24 cannot charge. The disabling may be positive (by actually removing the capacitor charger and/or delivery switch from operation) or negative (e.g., by omitting the software commands necessary to operate the capacitor charger and/or delivery switch). This feature minimizes the likelihood that the defibrillator will accidentally deliver a shock when in training mode.

The details of a defibrillator training mode implemented according to this invention depend in part on the defibrillator design and in part on local defibrillator user protocols. The following description describes the use of the invention for one particular defibrillator design and for one particular user protocol. It should be understood, however, that the invention is not limited to this defibrillator design or to this user protocol.

A suitable defibrillator for use with this invention is disclosed in U.S. patent appl. Ser. No. 08/227,553, "Electrotherapy Method and Apparatus," filed Apr. 14, 1994, and U.S. patent appl. Ser. No. 08/240,272, "Defibrillator With Self-Test Features," filed May 10, 1994. The disclosures of these two patent applications are incorporated herein by reference. The following example illustrates the use of this invention with the defibrillator described in these two patent applications.

Figure 2:
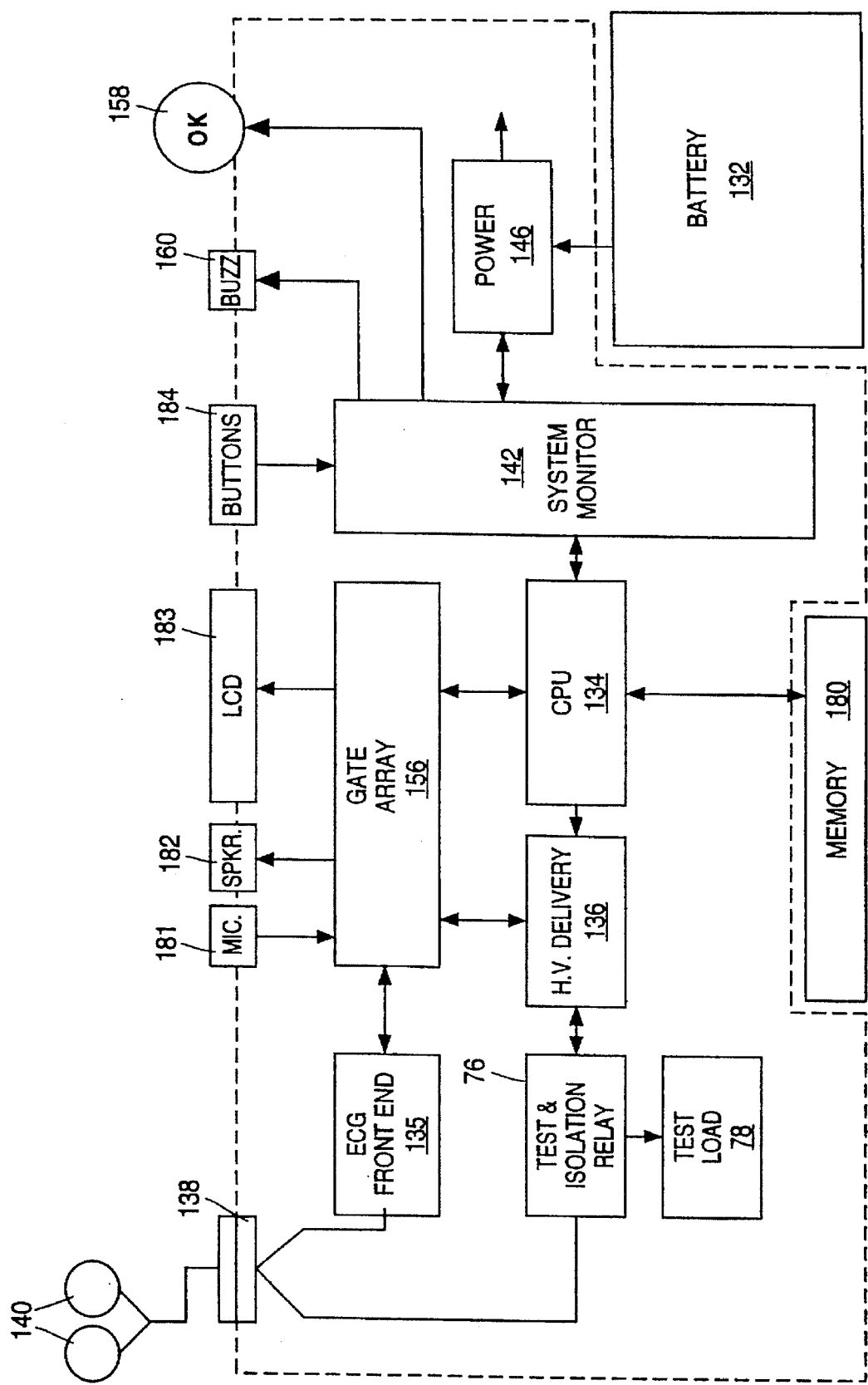
FIG. 2 is a schematic block diagram of a defibrillator implementing this invention.

FIG. 2 is a block diagram showing a preferred configuration for the defibrillator of this invention. As shown in FIG. 2, defibrillator 130 has a power source such as a removable battery 132, a controller such as CPU 134, and a high voltage delivery system 136 including a capacitor or capacitor bank and appropriate switches (not shown) to deliver a pulse of electrical energy to an electrode connector or interface 138 and then to a patient via electrodes 140. Delivery of the electrical pulse is controlled by CPU 134. A test and isolation relay 176 and a test load 178 are also provided.

An ECG front end system 135 acquires and preprocesses the patient's ECG signals through electrodes 140 and sends the signals to CPU 134 via a system gate array 156. System gate array 156 is a custom application specific integrated circuit (ASIC) that integrates many of the defibrillator's functions, such as display control and many of the instrument control functions, thereby minimizing the number of parts and freeing up main CPU time for use in other tasks. The system gate array could be replaced by discrete logic and/or another CPU, of course, as known in the art.

The defibrillator shown in FIG. 2 also has a memory device 180 (e.g., a removable PCMCIA card), a microphone 181, a speaker 182, a LCD panel 183 and illuminated push-button controls 184.

A system monitor 142 mediates the defibrillator's self-testing functions by watching for scheduled test times and unscheduled power-on events. The system monitor generates test signals periodically at scheduled times and in response to specified events. The system monitor is also responsible for operating a fail-safe defibrillator status indicator or display 158. The system monitor communicates test signals to the CPU via a communication channel, and the CPU controls and gathers information from tested defibrillator components via other communication channels, some of which pass through system gate array 156.

Figure 3:
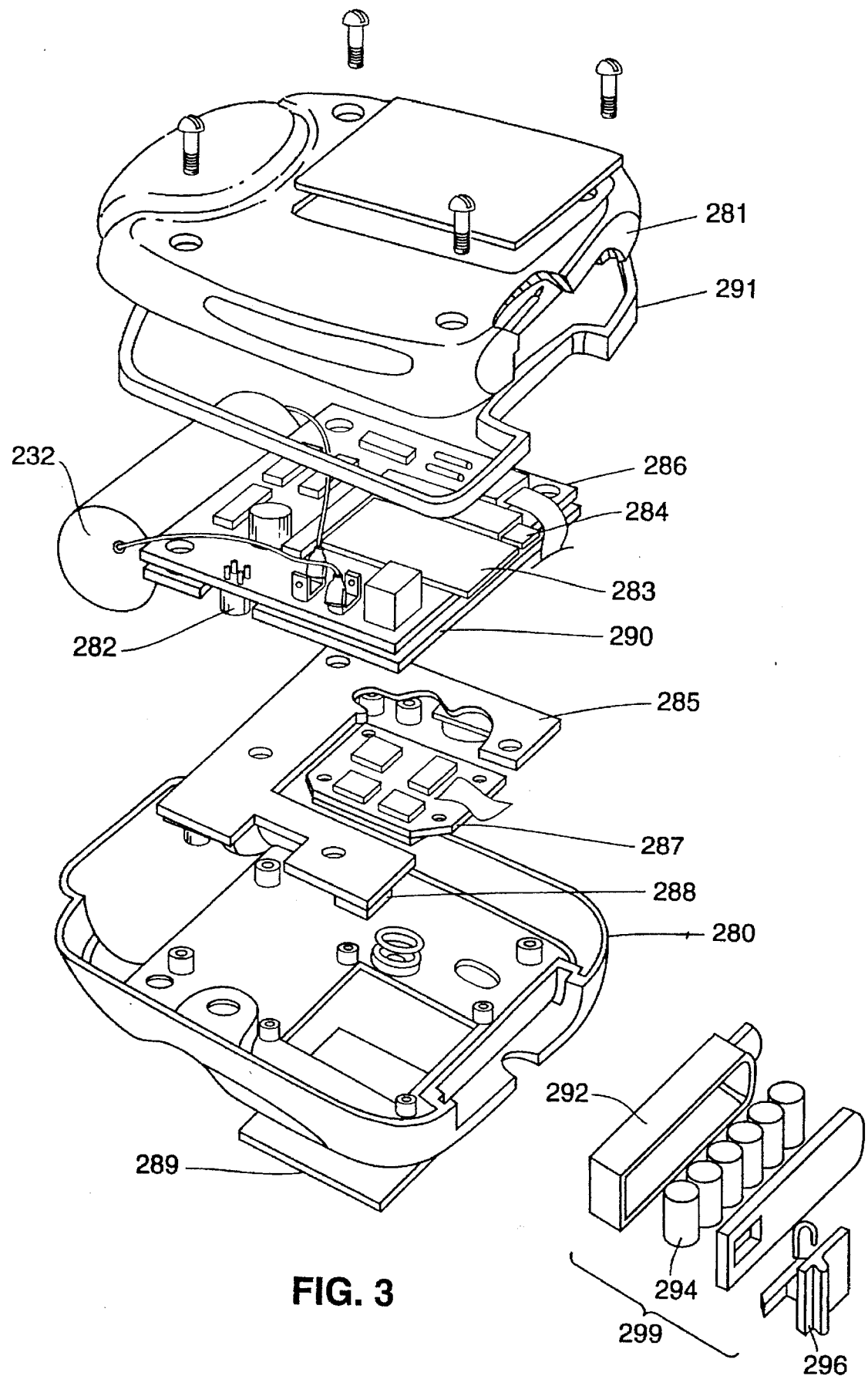
FIG. 3 is an exploded view of the defibrillator shown schematically in FIG. 2.
Figure 4:
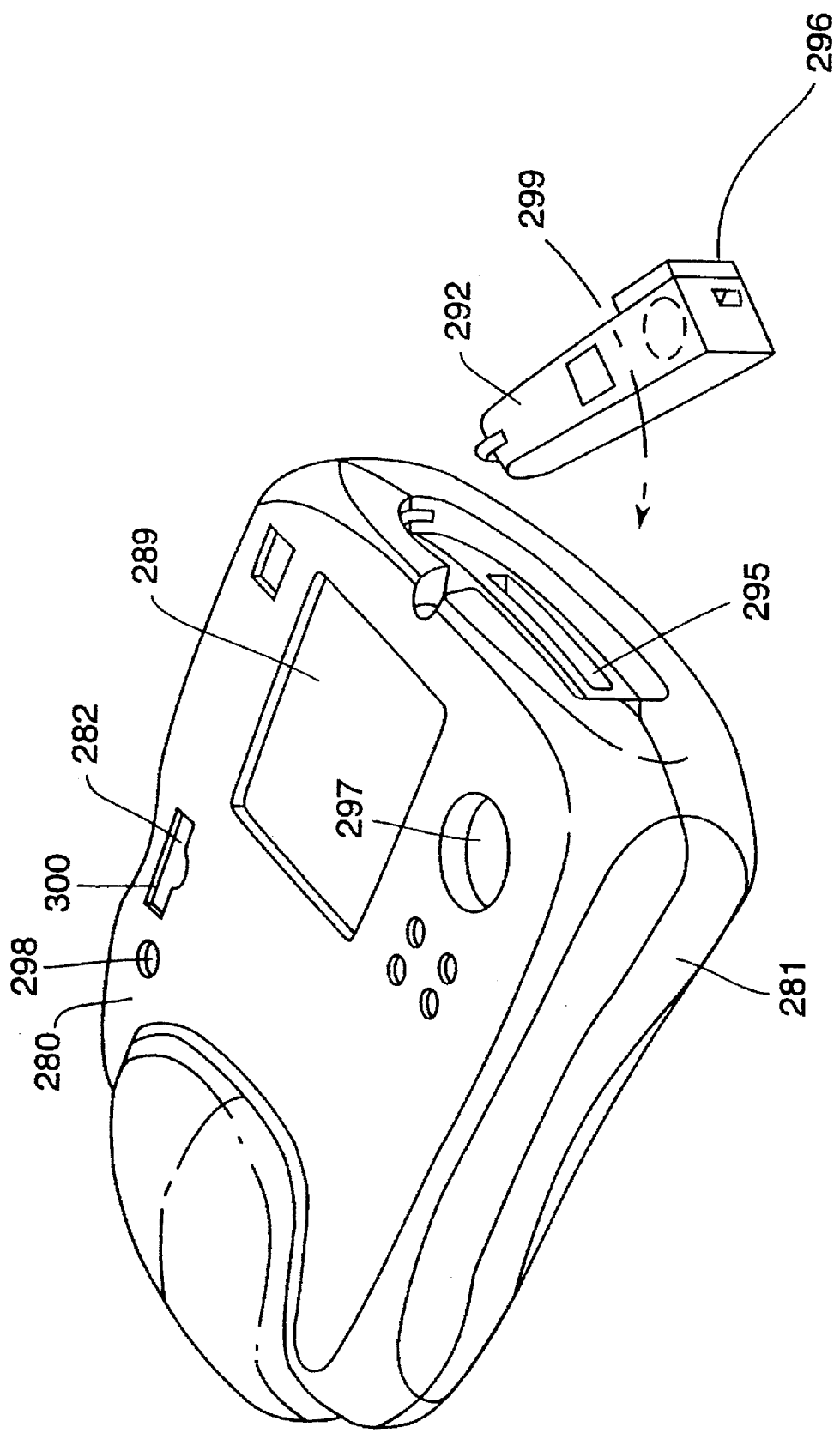
FIG. 4 is a perspective view of the defibrillator shown schematically in FIG. 2 and shown in an exploded view in FIG. 3.

FIGS. 3 and 4 show an implementation of the defibrillator shown schematically in FIG. 2. The defibrillator includes a molded two-part plastic housing with an upper case 280 and a lower case 281. A main printed circuit board ("PCB") 286 supports a capacitor 232 (part of the high voltage delivery system 136 of FIG. 2), an electrode connector 282 (electrode interface 138 of FIG. 2), a PCMCIA memory card 283 (corresponding to memory device 186 of FIG. 2) and a PCMCIA memory card ejector mechanism 284. The PCMCIA memory card 283 lies within a PCMCIA memory card slot 295 on PCB 286.

A keyboard PCB 285 and a display PCB 287 are disposed between the main PCB 286 and the upper case 280. Keyboard PCB 285 interfaces with the defibrillator's operator buttons 297 and 298 (the illuminated push-button control 184 of FIG. 2), and display PCB 287 operates the defibrillator's LCD display 288 (element 183 of FIG. 2). A display window 289 in the upper case permits display 288 to be seen by an operator.

A battery assembly 299 (corresponding to battery 132 of FIG. 2) consisting of a battery housing 292 and six lithium-manganese dioxide primary cells 294 is disposed in upper case 280 so that the batteries are in electrical contact with the capacitor charge circuits and other circuits of main PCB 286. The battery assembly has a latching mechanism 296 for attaching and detaching the battery assembly to and from the defibrillator.

The location of the battery assembly in front of the PCMCIA memory card slot prevents the defibrillator operator or others from accessing the PCMCIA card while the defibrillator is powered up and operating. This arrangement protects the operator and patient from accidental shocks and protects the defibrillator itself from damage caused by inadvertent removal of the PCMCIA card during operation.

The defibrillator shown in FIGS. 2–4 has features that make it easier to train users in training mode and therefore easier to use in patient treatment mode. These features will be explained in the context of operating the defibrillator in a semi-automatic operating mode to treat a patient.

Semi-automatic mode may be entered by depressing on/off button 298. After any power-on self-tests (e.g., as described in Ser. No. 08/240,272), the defibrillator displays its operational status on display 288. If the defibrillator is operational, it begins charging its capacitor and proceeds to electrode analysis.

Figure 5:
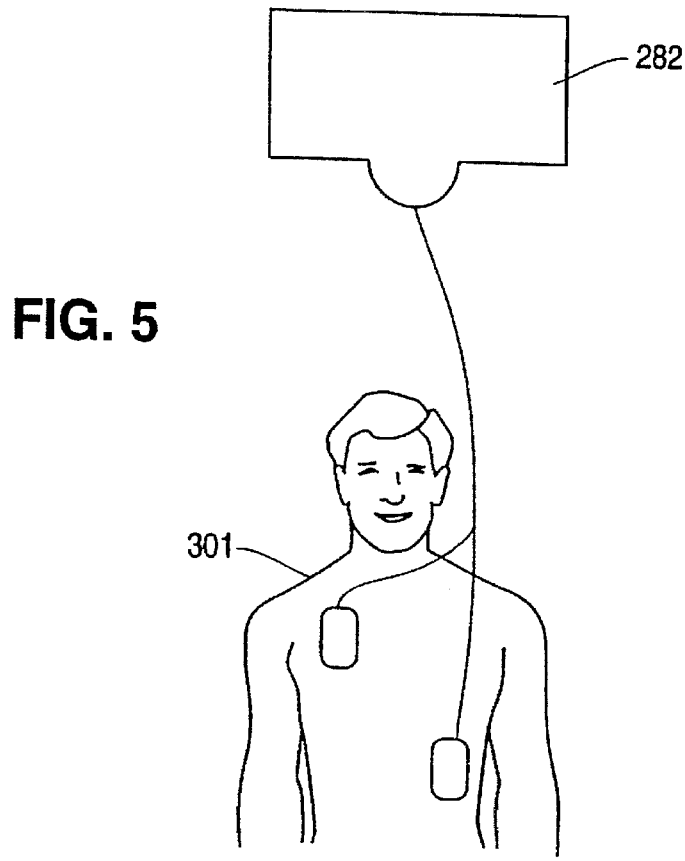
FIG. 5 is a detail of an icon used in connection with the defibrillator shown in FIGS. 3 and 4.

If the defibrillator determines that electrodes have not yet been attached to electrode connector 282, display 288 tells the user (such as with an "Attach Pads" message) and a light 300 adjacent the connector begins flashing to show the user where the electrodes connect to the defibrillator. In addition, the electrode connector is marked with connection icon 301, as shown in FIG. 5, to help guide the user to the electrode connector and to show the user how to place the electrodes on the patient. If the electrodes are attached but are not operational for some reason (as determined by any electrode attachment test known in the art), the defibrillator displays a message such as "Replace Pads" on display 288. The "Attach Pads" and "Replace Pads" or other visual messages may be accompanied by voice prompts from the defibrillator.

Once the electrodes have been attached and have been determined by the defibrillator to be operational (in a manner outside the scope of the present invention), the defibrillator begins analyzing the patient's ECG to make "shock" or "no shock" decisions in a manner known in the art. In this state, the defibrillator displays an "Analyzing" or similar message on display 288. The defibrillator may also analyze the quality of the ECG information it is receiving and will display a message such as "Analyzing Stopped" (possibly accompanied by a voice prompt) if a suspected motion artifact (or other artifact) appears in the ECG signal.

If the defibrillator makes three consecutive "no shock" decisions according to its analysis protocol, the defibrillator displays "No Shock Advised" or a similar message on display 288 and continues monitoring. If, however, the defibrillator makes a "shock" decision, it immediately completes charging its capacitor and displays a message such as "Prepare To Shock." These visual messages may be accompanied by voice prompts. In addition, the defibrillator preferably emits a tone during capacitor charging, with the pitch of the tone rising as the charging nears completion.

The defibrillator becomes armed when the capacitor is fully charged. The defibrillator indicates this condition with illuminated shock button 297 and both visual and voice prompting: first, "Prepare To Shock—Stand Clear", then "Shock Advised—Press To Shock" or similar messages. In addition, a continuous tone alternates with the voice prompts. The user delivers a shock to the patient by depressing shock button 297. After delivery of a shock, the defibrillator emits a "Shock Delivered" (or its equivalent) visual and/or voice prompt, then transitions to an analysis state.

The user may disarm the device by depressing on/off button 298.

After delivering a number shocks (with the number being programmable), the defibrillator of this embodiment pauses to permit CPR to be performed on the patient. The length of the pause is programmable by the user. During the pause, the defibrillator display 288 shows the message "Attend Patient" and the time remaining in the pause.

In addition to the CPR pause, the defibrillator may have a pause button (such as one of the buttons 184 in FIG. 2) that places the defibrillator in a pause state for a period of time. In the pause state: all audible prompts are disabled; if the defibrillator had been charging, it stops charging; if the defibrillator had been armed, it disarms; and the defibrillator returns to a precharged state. The pause state ends when the pause button is hit again or at the end of the pause period. The length of the pause period may be programmable.

The defibrillator display 288 may show real time patient ECG waveforms, heartrate, number of shocks delivered, elapsed time, defibrillator condition (e.g., low battery warning) and any other relevant information. The defibrillator may also be able to display data from earlier uses in an Event Review mode.

Similar defibrillator operations may be provided for automatic and manual operation of the defibrillator.

According to this invention, the defibrillator's training mode simulates the defibrillator's operation modes. To enter training mode, the user removes battery assembly 299, inserts a PCMCIA training card in PCMCIA slot 295, and replaces the battery assembly. This act activates the initial training sequence. In training mode, software on the PCMCIA card controls operation of the defibrillator; the code controlling treatment mode becomes unavailable. The training software does not operate the capacitor charging circuit and or the high voltage delivery circuit, so that the defibrillator's ability to deliver a shock is effectively disabled.

In addition, the defibrillator displays a "Training Mode" message continually while in training mode. Thus, because the training code is on the training card, and because the training card advertises its presence within the defibrillator, there is very little chance a user would attempt to treat a patient with the defibrillator while it is in training mode. If the defibrillator's battery is dead or absent and the user inserts a new battery while the training card is inserted, the defibrillator will power up and display its "Training Mode" message and will tell the user that the training card must be removed in order to leave training mode.

The preferred embodiment offers a choice among multiple training scripts, each made up of sequences of ECG rhythms, such as ventricular fibrillation, fine ventricular fibrillation, ventricular tachycardia, normal sinus, normal sinus to ventricular fibrillation transition, and asystole. The desired script may be chosen by the trainee or by an instructor before the defibrillator is turned over to the trainee. The trainee begins the script by pressing the on/off button 298, and the defibrillator guides the trainee through the script using the audible and visual prompts the defibrillator would use in when actually treating a patient, such as those described above. The training script would most likely include a shock recommendation from the defibrillator followed by actuation of the shock delivery button by the trainee. The trainee may exit training mode by removing the battery and PCMCIA training card from the defibrillator.

The script may be placed on the training cards by a certification or training authority. Alternatively, a trainer or other user may design personalized training scripts of portions of training scripts.

The training mode of this invention may be performed with or without attaching the defibrillator electrodes to the defibrillator or to a conductive surface, as determined by the selected script. For example, the trainee could select a script option in which attachment of the electrodes is assumed.

In the preferred embodiment, the defibrillator provides training on maintenance functions as well as treatment functions. For example, one or more of the training scripts provide instruction on steps to follow when the defibrillator displays a low battery warning or if the defibrillator indicates that some other self-test has failed.

The training card may be provided With a memory for recording the trainee's actions in response to the training script, such as the way the trainee operated the defibrillator's controls. This information may be used to evaluate the trainee's performance, for example by comparing the trainee's operation of the defibrillator with preset operation standards. Alternatively, the memory used for this training evaluation function may be located within the defibrillator itself and not part of the training card.

Certain defibrillator use protocols require users to fill out "run reports" detailing the condition of the patient and the treatment applied using the defibrillator. The operator training course could include the use of run reports filled out after a training session. If the training card has memory to record the training session as discussed above, the training card and run report may be submitted for evaluation by a certification authority. In fact, training could be initiated and evaluated from a remote location by mailing a training card to a trainee and receiving back the results (e.g., training card and run report) of the training session.

The preferred embodiment above was discussed primarily in connection with a particular semi-automatic defibrillator configured to operate according to a particular protocol. Other defibrillators, other protocols and other defibrillator training scenarios may be used, of course, without departing from the scope of this invention.

For example, in the preferred embodiment, the device shows that it is in training mode by displaying an appropriate message. This feature is important to prevent a user from attempting to treat a patient while the device is in training mode. Other ways of identifying training mode are possible, of course, such as a ribbon or marker extending from the training card; a mechanical flag that displays only during training mode; or a light or other electronic indicator that displays only during training mode.

In another alternative embodiment, the defibrillator could be switched to training mode by inserting a special training battery instead of by inserting a training card. Also, training mode could be initiated by a switch or other control on the defibrillator.

In the preferred embodiment, all training code is on the training card. In alternative embodiments, the training code could be contained within the defibrillator itself.

We claim:

1. A method for a user to operate an automatic or semiautomatic external defibrillator to treat a patient, the method comprising the following steps:

providing an automatic or semiautomatic external defibrillator to the user;

activating the defibrillator to provide therapy to the patient;

placing the defibrillator in a pause state by the user actuating a pause actuator;

ending the pause state.

2. The method of claim 1 wherein the placing step comprises disabling defibrillator audible prompts.

3. The method of claim 1 wherein the activating step comprises charging an energy source and the placing step comprises ceasing charging of the energy source.

4. The method of claim 1 wherein the activating step comprises arming the defibrillator and the placing step comprises disarming the defibrillator.

5. The method of claim 1 wherein the ending step comprises the user actuating a defibrillator actuator.

6. The method of claim 1 wherein the placing step comprises the user actuating a button on the defibrillator.

7. The method of claim 6 wherein the ending step comprises the user actuating the button.

8. The method of claim 1 wherein the ending step comprises ending the pause state after a predetermined pause period.

9. The method of claim 8 further comprising programming the predetermined pause period's length.

* * * * *

UNITED STATES PATENT AND TRADEMARK OFFICE
CERTIFICATE OF CORRECTION

PATENT NO. :     5,662,690

DATED       :     Sep. 2, 1997

INVENTOR(S):    Clinton Cole , Carlton B. Morgan, Judi Cyrus, Daniel Powers

It is certified that error appears in the above-identified patent and that said Letters Patent is hereby corrected as shown below:

In column 1, line 28, please change "patient instead" to — patient. Instead —.

In column 4, line 17, please change "a" (second occurrence) to — an —.

In column 4, line 38, please change "186" to — 180 —.

In column 5, line 57, please insert "of" after "number" (first occurrence).

In column 6, line 23, please insert "/" after "and".

In column 6, line 46, please delete "in".

In column 6, line 54, please change "of" to — or —.

In column 7, line 1, please change "With" to — with —.

Signed and Sealed this

Seventh Day of April, 1998

Attest:

BRUCE LEHMAN

*Attesting Officer*    *Commissioner of Patents and Trademarks*